United States Patent
Kenany

(10) Patent No.: US 9,112,447 B2
(45) Date of Patent: Aug. 18, 2015

(54) NANO POWER CELL AND METHOD OF USE

(75) Inventor: Saad Al Kenany, Palo Alto, CA (US)

(73) Assignee: SOLERA LABORATORIES, INC., Palo Alto, CA (US)

( * ) Notice: Subject to any disclaimer, the term of this patent is extended or adjusted under 35 U.S.C. 154(b) by 1101 days.

(21) Appl. No.: 11/934,283

(22) Filed: Nov. 2, 2007

(65) Prior Publication Data

US 2008/0128842 A1 Jun. 5, 2008

Related U.S. Application Data

(60) Provisional application No. 60/856,547, filed on Nov. 3, 2006.

(51) Int. Cl.
| | | |
|---|---|---|
| H01L 31/0248 | (2006.01) | |
| H01L 31/0352 | (2006.01) | |
| H01L 31/04 | (2014.01) | |
| H01L 31/06 | (2012.01) | |
| H02S 10/30 | (2014.01) | |

(52) U.S. Cl.
CPC ............ *H02S 10/30* (2013.01); *H01L 31/0352* (2013.01); *A61B 2560/0214* (2013.01); *Y02E 10/50* (2013.01)

(58) Field of Classification Search
USPC ........... 136/250, 252, 261, 262; 257/428, 431
See application file for complete search history.

(56) References Cited

U.S. PATENT DOCUMENTS

| | | | | |
|---|---|---|---|---|
| 4,021,323 A | * | 5/1977 | Kilby et al. ................... 136/246 |
| 4,032,477 A | * | 6/1977 | Gratzel ....................... 252/501.1 |
| 4,367,131 A | * | 1/1983 | Gratzel et al. ........... 204/157.52 |
| 4,381,978 A | * | 5/1983 | Gratzel et al. ................. 205/340 |
| 4,382,846 A | * | 5/1983 | Gratzel et al. .............. 204/157.5 |
| 4,389,290 A | * | 6/1983 | Gratzel et al. ................. 205/340 |
| 4,394,293 A | * | 7/1983 | Gratzel et al. ................. 502/159 |
| 4,421,617 A | * | 12/1983 | Gratzel et al. ........... 204/157.52 |
| 4,847,231 A | * | 7/1989 | Gratzel et al. ................... 502/74 |
| 4,927,721 A | * | 5/1990 | Gratzel et al. ................. 429/111 |
| 5,084,365 A | * | 1/1992 | Gratzel et al. ................. 429/111 |
| 5,223,634 A | * | 6/1993 | Gratzel et al. ................. 556/137 |
| 5,378,628 A | * | 1/1995 | Gratzel et al. ........... 204/403.14 |
| 5,393,903 A | * | 2/1995 | Gratzel et al. ................. 556/137 |
| 5,441,827 A | * | 8/1995 | Gratzel et al. ................. 429/111 |
| 5,482,570 A | * | 1/1996 | Saurer et al. ................... 136/255 |
| 5,728,487 A | * | 3/1998 | Gratzel et al. ................. 429/111 |
| 5,789,592 A | * | 8/1998 | Gratzel et al. ................... 546/21 |
| 6,024,807 A | * | 2/2000 | Pappas et al. .................. 148/513 |
| 6,067,184 A | * | 5/2000 | Bonhote et al. ............... 359/265 |
| 6,245,988 B1 | * | 6/2001 | Gratzel et al. ................. 136/263 |
| 6,335,480 B1 | * | 1/2002 | Bach et al. ..................... 136/263 |
| 6,426,827 B1 | * | 7/2002 | Bonhote et al. ............... 359/265 |
| 6,706,963 B2 | * | 3/2004 | Gaudiana et al. ............. 136/263 |
| 6,734,305 B2 | * | 5/2004 | Pierre et al. ................... 544/347 |

(Continued)

OTHER PUBLICATIONS

McGraw-Hill Concise Encyclopedia of Physics. © 2002 by The McGraw-Hill Companies, Inc., downloaded from <ahref="http://encyclopedia2.thefreedictionary.com/Photovoltaic+effect">Photovoltaic effect</a>, 2 pages, author unkown.*

(Continued)

*Primary Examiner* — Evan Pert
(74) *Attorney, Agent, or Firm* — DLA Piper LLP (US)

(57) ABSTRACT

A nano power cell and method of use are described wherein the nano power cell absorbs electromagnetic energy is nano particles in an optical fluid that flow in microchannels of the nano power cell.

18 Claims, 5 Drawing Sheets

(56) References Cited

U.S. PATENT DOCUMENTS

| | | | |
|---|---|---|---|
| 6,858,158 B2* | 2/2005 | Chittibabu et al. | 252/183.11 |
| 6,900,382 B2* | 5/2005 | Chittibabu et al. | 136/256 |
| 6,913,713 B2* | 7/2005 | Chittibabu et al. | 252/501.1 |
| 6,924,427 B2* | 8/2005 | Eckert et al. | 136/252 |
| 6,933,436 B2* | 8/2005 | Shaheen et al. | 136/263 |
| 6,949,400 B2* | 9/2005 | Ryan | 438/64 |
| 7,022,910 B2* | 4/2006 | Gaudiana et al. | 136/256 |
| 7,094,441 B2* | 8/2006 | Chittibabu et al. | 427/74 |
| 7,186,911 B2* | 3/2007 | Ryan | 136/263 |
| 7,196,834 B2* | 3/2007 | Brabec et al. | 359/245 |
| 7,205,473 B2* | 4/2007 | Li et al. | 136/263 |
| 7,220,914 B2* | 5/2007 | Chittibabu et al. | 136/263 |
| 7,259,324 B2* | 8/2007 | Zeira | 136/263 |
| 7,304,361 B2* | 12/2007 | Brabec et al. | 257/431 |
| 7,306,968 B2* | 12/2007 | Brabec et al. | 438/99 |
| 7,329,709 B2* | 2/2008 | Gaudiana et al. | 525/403 |
| 7,351,907 B2* | 4/2008 | Gaudiana et al. | 136/263 |
| 7,407,831 B2* | 8/2008 | Brabec et al. | 438/99 |
| 7,413,997 B2* | 8/2008 | Brabec et al. | 438/758 |
| 7,414,188 B2* | 8/2008 | Gaudiana et al. | 136/263 |
| 7,466,376 B2* | 12/2008 | Galvin et al. | 349/84 |
| 7,476,278 B2* | 1/2009 | Brabec et al. | 118/718 |
| 7,522,329 B2* | 4/2009 | Brabec et al. | 359/265 |
| 7,544,747 B2* | 6/2009 | Gaudiana et al. | 525/445 |
| 7,994,422 B2 | 8/2011 | Jin et al. | |
| 8,319,092 B1* | 11/2012 | Kenany et al. | 136/250 |
| 8,574,463 B2 | 11/2013 | Tani et al. | |
| 2003/0188776 A1* | 10/2003 | Li et al. | 136/244 |
| 2003/0188777 A1* | 10/2003 | Gaudiana et al. | 136/263 |
| 2003/0189402 A1* | 10/2003 | Gaudiana et al. | 313/507 |
| 2003/0192583 A1* | 10/2003 | Ryan | 136/244 |
| 2003/0192584 A1* | 10/2003 | Beckenbaugh et al. | 136/256 |
| 2003/0192585 A1* | 10/2003 | Beckenbaugh et al. | 136/263 |
| 2004/0025933 A1* | 2/2004 | Chittibabu et al. | 136/263 |
| 2004/0025934 A1* | 2/2004 | Chittibabu et al. | 136/263 |
| 2004/0031520 A1* | 2/2004 | Ryan | 136/263 |
| 2005/0039790 A1* | 2/2005 | Chittibabu et al. | 136/252 |
| 2005/0040374 A1* | 2/2005 | Chittibabu et al. | 252/501.1 |
| 2005/0045851 A1* | 3/2005 | He et al. | 252/62.3 R |
| 2005/0067006 A1* | 3/2005 | Eckert et al. | 136/244 |
| 2005/0189014 A1* | 9/2005 | Gaudiana et al. | 136/256 |
| 2005/0211292 A1* | 9/2005 | Chittibabu et al. | 136/263 |
| 2005/0279399 A1* | 12/2005 | Gaudiana et al. | 136/243 |
| 2006/0003217 A1* | 1/2006 | Cohen et al. | 429/34 |
| 2006/0093017 A1* | 5/2006 | Gong et al. | 375/134 |
| 2006/0278890 A1* | 12/2006 | Brabec et al. | 257/186 |
| 2007/0012349 A1* | 1/2007 | Gaudiana et al. | 136/244 |
| 2007/0089779 A1* | 4/2007 | Balasubramanian et al. | 136/252 |
| 2007/0102040 A1* | 5/2007 | Beckenbaugh et al. | 136/263 |
| 2007/0107776 A1* | 5/2007 | Li et al. | 136/263 |
| 2007/0131277 A1* | 6/2007 | Gaudiana et al. | 136/258 |
| 2007/0181179 A1* | 8/2007 | Brabec et al. | 136/263 |
| 2007/0193621 A1* | 8/2007 | Brabec et al. | 136/246 |
| 2007/0246094 A1* | 10/2007 | Brabec et al. | 136/244 |
| 2007/0251570 A1* | 11/2007 | Eckert et al. | 136/256 |
| 2007/0267055 A1* | 11/2007 | Gaudiana et al. | 136/244 |
| 2007/0289626 A1* | 12/2007 | Brabec et al. | 136/263 |
| 2007/0295400 A1* | 12/2007 | Brabec et al. | 136/263 |
| 2008/0006324 A1* | 1/2008 | Berke et al. | 136/263 |
| 2008/0011352 A1* | 1/2008 | Zeira | 136/256 |
| 2008/0087324 A1* | 4/2008 | Gaudiana et al. | 136/261 |
| 2008/0121281 A1* | 5/2008 | Gaudiana et al. | 136/263 |
| 2009/0050207 A1* | 2/2009 | Galvin et al. | 136/263 |
| 2010/0218825 A1 | 9/2010 | Jee et al. | |

OTHER PUBLICATIONS

Author Unknown, Downloaded from "Answers.com", "Does electromagnetic radiation consist of photons?", 2 pages, downloaded from http://wiki.answers.com/Q/Does_electromagnetic_radiation_consist_of_photons, Jul. 2011.*

Author Unknown, Downloaded from "NEWTON, Ask a Scientist at Argonne National Labs: Does a photon have a charge?", 2 pages, downloaded from http://newton.dep.anl.gov/askasci/phy99/phy99552.htm, 1999.*

Institute of Electrical and Electronics Engineers (IEEE): Dictionary.com, "electromagnetic radiation," in Collins English Dictionary—Complete & Unabridged 10th Edition. Source location: HarperCollins Publishers. http://dictionary.reference.com/browse/electromagnetic radiation. Available: http://dictionary.reference.com. Accessed: Oct. 4, 2012.*

Institute of Electrical and Electronics Engineers (IEEE): Dictionary.com, "photon," in Collins English Dictionary—Complete & Unabridged 10th Edition. Source location: HarperCollins Publishers. http://dictionary.reference.com/browse/photon. Available: http://dictionary.reference.com. Accessed: Oct. 4, 2012.*

Institute of Electrical and Electronics Engineers (IEEE): Dictionary.com, "conservation of charge," in Collins English Dictionary—Complete & Unabridged 10th Edition. Source location: HarperCollins Publishers. http://dictionary.reference.com/browse/conservation of charge. Available: http://dictionary.reference.com. Accessed: Oct. 4, 2012.*

Princeton University, Open Source Radiation Safety Training—Module 1: Radiation Properties, 13 pages, downloaded Oct. 4, 2012, http://web.princeton.edu/sites/ehs/osradtraining/radiationproperties/radiationproperties.htm.*

PCT/US07/23316 International Search Report, dated Oct. 6, 2008.
PCT/US07/23316 Written Opinion, dated Oct. 6, 2008.

* cited by examiner

NANO POWER CELL AND METHOD OF USE

PRIORITY CLAIM

This application claims priority under 35 USC 119(e) to U.S. Provisional Patent Application Ser. No. 60/856,547 filed on Nov. 3, 2006 and entitled "Nano Power Cell and Method of Use", the entirety of which is incorporated herein by reference.

FIELD

A nano power cell is described.

DETAILED DESCRIPTION OF ONE OR MORE EMBODIMENTS

A nano power cell is described that has a channel and that uses nano particles and an optical fluid flowing in the channel(s) to absorb electromagnetic radiation, such as infrared or visible radiation, and generate energy that can be used to power various devices. In one example of the use of the nano power cell below, the nano power cell may be used to power a medical device and it is in this context that the nano power cell is described. However, the nano power cell may be used to power other devices, such as cellular/mobile phone in which solar and/or infrared energy is used to generate the power. The nano power cell may be to power any other device that needs electrical power to operate, such as iPods, MP3 players, night vision goggles, handheld devices and the like. In other embodiments, the nano power cell may generate energy from infrared radiation, solar/visible light radiation or both solar and infrared radiation wherein the nano power cell may include infrared and solar/visible radiation sensitive nano particles. The nano power cell can also be used for any other device in which it is desirable to provide power for the device. In addition, the nano power cell may further include a power storage unit that may be attached or integrated with the nano power cell. In addition, the heat generated by the device, such as the cellular/mobile phone, computer, etc. which is powered by the nano power cell may be fed back to the nano power cell so that the nano power cell can generate some power from the heat generated by the device. Now, an example of the use of the nano power cell to power an implanted medical device is described in more detail.

Figure 1:
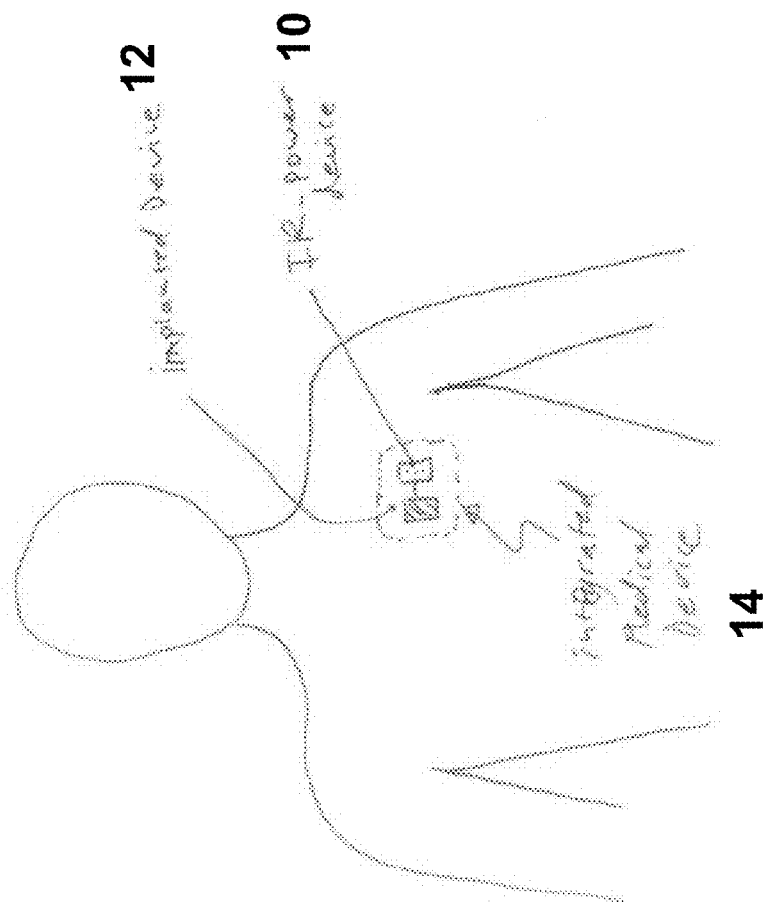
FIG. 1 illustrates an example of the use of a nano power cell.

FIG. 1 illustrates an example of the use of a nano power cell 10 wherein the power cell is powered by infrared energy such as the heat generated by a human body. Thus, the power cell 10 can be coupled to a medical device 12 to form an integrated medical device 14. The power cell, using the infrared energy (heat) of the human body in which the integrated medical device is implanted, generates power that is used to power the medical device. Thus, the integrated medical device 14 does not require an external power source nor an implanted power source that must be periodically removed from the human body and replaced when the power source is exhausted. This use of the nano power cell 10 is merely an example of the use of the power cell since it can be used with any device in which it is desirable to be able to provide power to the device using a power cell that generates energy from any type of electromagnetic energy, such as infrared energy, visible solar energy and the like.

Figure 2:
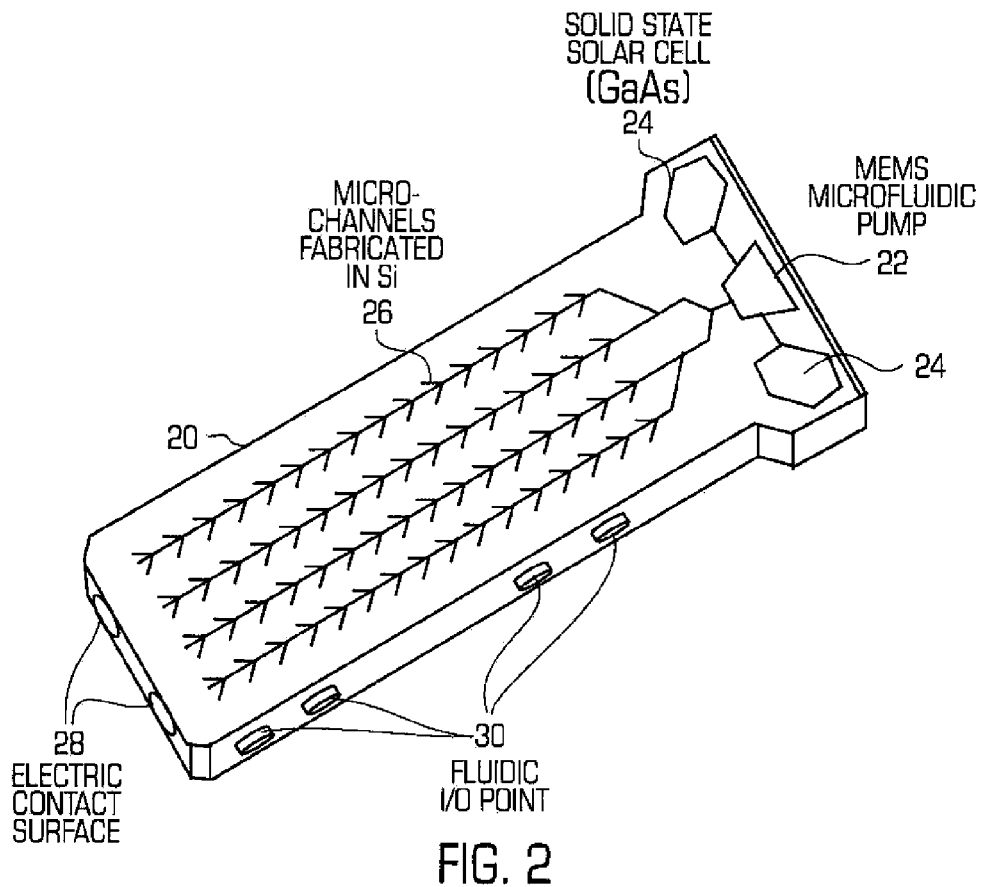
FIG. 2 illustrates an embodiment of a nano power cell.
Figure 5:
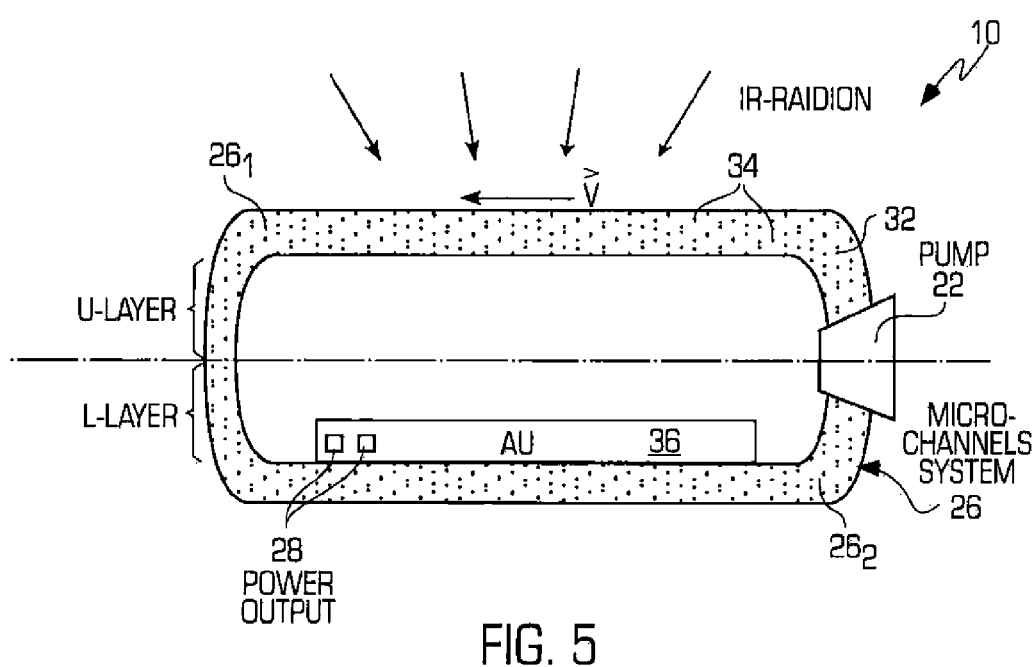
FIG. 5 illustrates a cutaway side view of the nano power cell shown in FIG. 1.

FIG. 2 illustrates an embodiment of a nano power cell 10. The cell may include a substrate/housing 20, that may be made of silicon is one embodiment, that may be multi-layered. The housing 20 may house a micro-electro-mechanical systems (MEMS) nano pump 22 that is coupled to one or more energy generation cells 24, such as infrared sensitive cells made of Gallium Arsenide (GaAs) that provides initial start-up power to the pump 22. In an embodiment in which the nano power cell is used with a device that is not implanted into a human being, the energy generation cells 24 may be solar cells or other cells that are capable of generating the initial start-up power for the pump 22. The pump 22 may further be coupled to one or more sets of microchannels 26 that are formed in the housing such as by fabricating the microchannels in the silicon using a well known process. In one exemplary embodiment, there may be an upper microchannel level and a lower microchannel level as shown in FIG. 5 which will be described below in more detail. The pump 22 may circulate a fluid, such as an optical fluid that may be commercially available LS-5238, through the microchannels and back to the pump wherein the fluid may be a fluid with nano-sized particles in the fluid that are sensitive to the electromagnetic radiation, such as infrared, that strikes the nano particles in the microchannels. In one embodiment, the particles may be Gallium Arsenide (GaAs), Germanium (Ge), Indium Gallium Arsenide (InGaAs) and/or Indium Phosphide (InP). In operation, the fluid with the nano-sized particles circulates through the microchannels and, during that circulation, the particles absorb energy from the electromagnetic energy generated by the body wherein the energy is stored as an electrical charge in the particle. The speed/velocity of the fluid flowing through the microchannels is such that the particles each receive the optimal amount of energy while exposed to the electromagnetic energy. The optimal amount of energy is as much energy as each particle is able to store without overcharging the particles or having the particles exposed to the electromagnetic energy when the particle is already fully charged. The electrical charge on each particle is then transferred to an electrode in the power cell which may store the accumulated electrical charge.

Returning to FIG. 2, the power cell 10 may further comprise a set of electrical contacts 28 wherein the electrical energy from the power cell is output from the power cell 10 to a device, such as the implanted medical device 12 shown in FIG. 1. The power cell 10 may further comprise one or more fluidic input/output ports 30 that permit the fluid with the nanoparticles to be added or removed from the power cell. Because microchannels are used in the power cell, there is a larger surface area of the microchannels which in turn means that there is more exposure of the particles to the electromagnetic radiation. In addition, the nanoparticles have a larger surface area that a larger particle occupying the same volume that further increases the amount of absorption of the electromagnetic energy by the power cell. In addition, the flow of the particles in the fluid results in the constant charge and discharge of the electromagnetic energy carrying particles so that a charge/recharge cycle typical with cells with fixed energy absorption cells in not required. In order words, the power cell 10 does not have a typical discharge time associated with it during which the user must wait for the fixed cells to be discharged before recharging the cell. The particles in the fluid are also exposed to radiation on all sides of the particle since the orientation of the particle to the radiation source in the fluid is not fixed and changes constantly. Thus, the power cell 10 has a higher efficiency than typical power cells.

Figure 3:
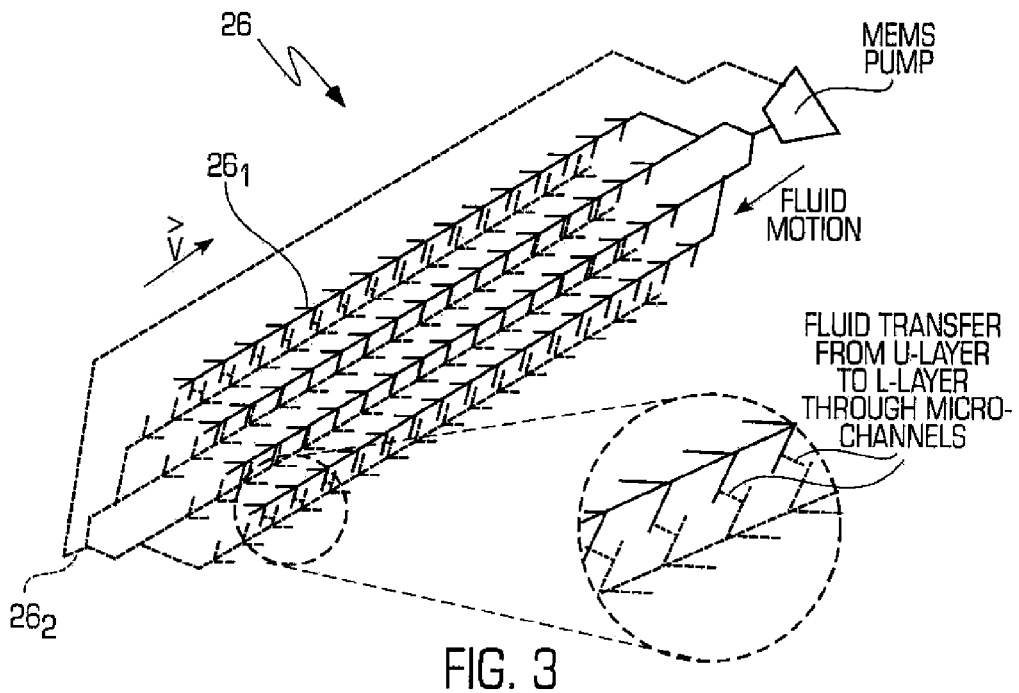
FIGS. 3 and 4 illustrate further details of the nano power cell.
Figure 4:
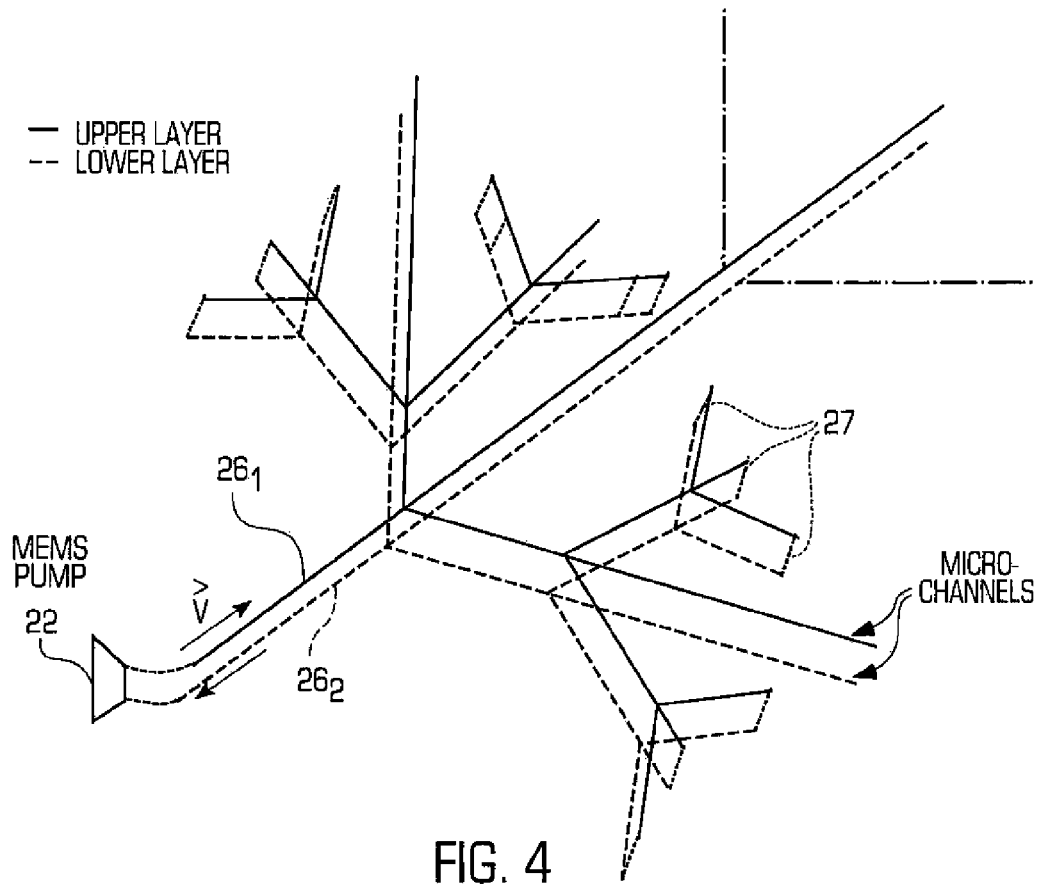

FIGS. 3 and 4 illustrate further details of the nano power cell. In particular, FIGS. 3 and 4 illustrate the microchannels 26 coupled to the pump 22 and in particular an upper level microchannel $26_1$ and a lower level microchannel $26_2$ that are vertically displaced from each other within the housing. As the fluid circulates through the microchannels (with the flow being away from the pump 22 through the upper level microchannels $26_1$ and then back to the pump through the lower level microchannels $26_2$) the fluid passes from the upper level microchannels to the lower level microchannels via capillaries 27 that connect the two microchannels at the end branches of the microchannels.

FIG. 5 illustrates a cutaway side view of the nano power cell 10 shown in FIG. 1 wherein the upper microchannels $26_1$ and the lower microchannels $26_2$ are shown connected to the pump 22 and connected to each other to form a fluid flow path. A fluid 32, such as an optical fluid, with nanoparticles 34 flow out from the pump through the upper microchannels $26_1$ and the back to the pump through the lower microchannels $26_2$. The nanoparticles may be 1 nanometer to 10 micrometers in size. The pump 22 generates a fluid velocity ($\bar{v}$) and therefore a particle velocity that is optimized to have a maximum charge absorbed by each particle in a minimum amount of time and then fully discharge the particles as described below. In particular, the velocity is optimized so that the particles spend just enough time in the upper microchannels $26_1$ exposed to the electromagnetic radiation in order to acquire a maximum charge without becoming overcharged. Once the particles are charged while traveling in the upper microchannels $26_1$ they transition into the lower microchannels $26_2$ where they come into contact with an plate 36, such as a gold plated silicon plate/electrode) where the particles discharge their charge onto the plate. As described above, the velocity ($\bar{v}$) of the fluid is optimized to permit the particles to full discharge in a minimum amount of time. The specific velocity ($\bar{v}$) for any particular nano power cell will depend on the fluid and particles used, the size of the microchannels, the type of electromagnetic radiation and the sensitivity of the nano particles to the particular type of electromagnetic radiation and the size of the plate and could be calculated by one of ordinary skill in the art.

Figure 6:
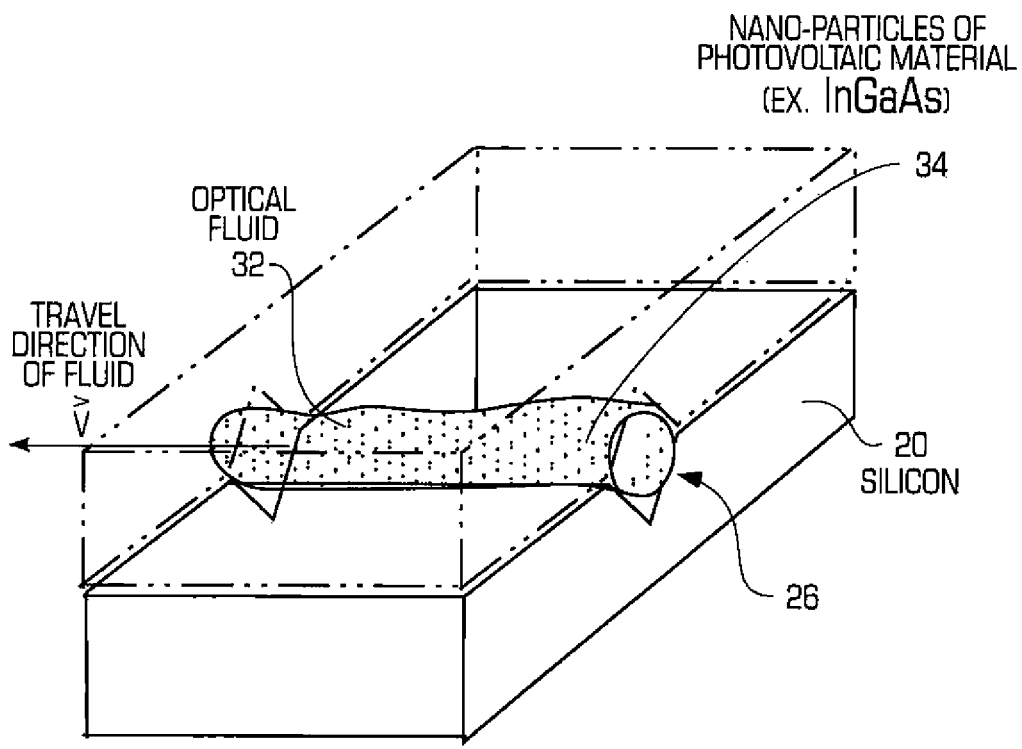
FIG. 6 illustrates a micro-channel that contains a fluid with nano-particles.

FIG. 6 illustrates a micro-channel 26 in the housing 20 that contains the fluid 32 with the plurality of nano-particles 34 that flow with a velocity ($\bar{v}$) within the fluid that is within the microchannel. The nano particles in the fluid in the microchannels result in a better energy absorption efficiency that other electromagnetic energy absorbing devices for various reasons. First, the microchannels have more surface area than typical channels and therefore expose more particles to the electromagnetic energy. Second, the nanoparticles, for a particle volume, have a larger surface area than a larger particle occupying the same volume as is well known. Third, the particles in the fluid are being constantly charged and discharged due to the fluid flow so they have a shorter charge/discharge cycle time that a fixed particle device. Fourth, since the particles rotate and move in the fluid, more of the surface area of each particle is exposed to the electromagnetic energy than with a fixed particle.

In another embodiment, the fluid may have infrared sensitive particles and visible sensitive particles mixed together so that the nano power cell can generate energy from the infrared energy as well as the visible electromagnetic energy during the circulation of the fluid in the nano power cell.

Figure 7:
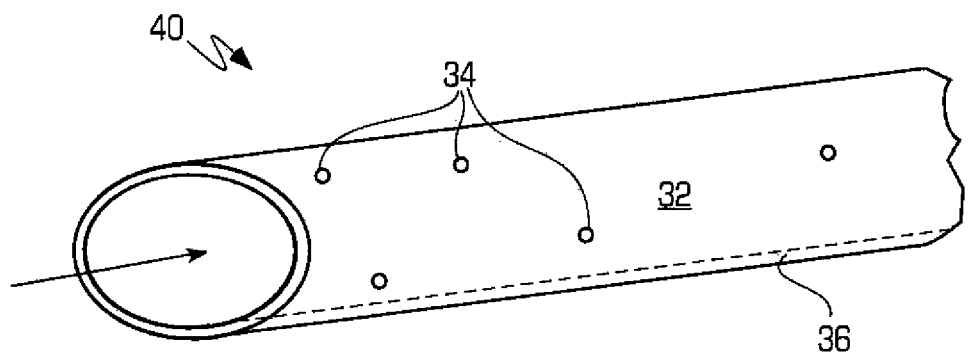
FIGS. 7-9 illustrate another embodiment of the nano power cell.
Figure 8:
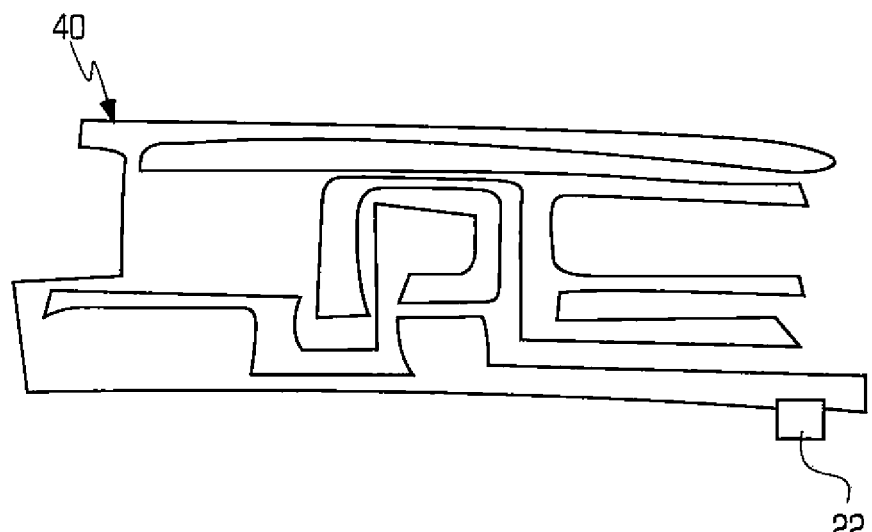
Figure 9:
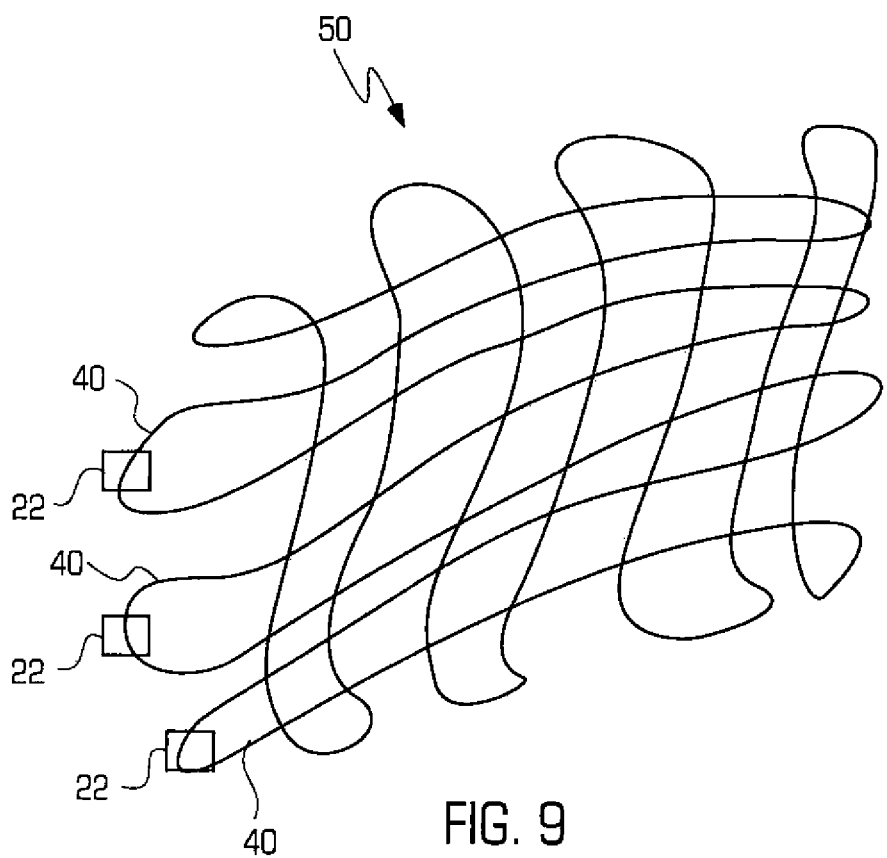

FIGS. 7-9 illustrate another embodiment of the nano power cell in the form of a fiber 40 or a thin transparent pipe (up to 125 microns) such an optical fiber that has an interior channel as shown in FIG. 7. The fiber 40 has the fluid 32, such as an optical fluid or a Photo-Voltaic-Nano-Materials (PVNM)-saturated optical fluid, with the nanoparticles 34 that flows through the fiber and contact a plate 36 (or a metallic coating inside of the hollow fiber or the thin transparent pipe) that is located inside that allows the nanoparticles to absorb energy and then discharge that energy to the plate as described above. FIG. 8 illustrates an example of a fiber with a particular exemplary pattern and the pump 22 that pumps the fluid with the nanoparticles through the fiber. The fiber as shown in FIGS. 7 and 8 may be used to make a fabric (as shown in FIG. 9) that creates flexible power generating structures in large areas that can be applied in any surface. As shown in FIG. 9, a piece of fabric 50 made with one or more fibers 40 may have one or more pumps 22 that circulate the fluid through the fibers 40. Thus, the entire piece of fabric becomes an energy generation device/system that can be made so that it covers a large surface area and generates energy from the electromagnetic radiation. Using the fiber shown in FIGS. 7-8, other devices/structures may also be formed that are made of or contain the fibers such as buildings, roofing shingles, the external surfaces of products and the like.

While the foregoing has been with reference to a particular embodiment of the invention, it will be appreciated by those skilled in the art that changes in this embodiment may be made without departing from the principles and spirit of the invention, the scope of which is defined by the appended claims.

The invention claimed is:

1. A nano power cell, comprising:
a substrate;
one or more microchannels formed in the substrate;
a pump that circulates a fluid through the microchannels;
the fluid containing a plurality of electromagnetically sensitive particles that receive a charge from an electromagnetic radiation source; and
an electrode within the substrate that receives the charge from the electromagnetically sensitive particles and outputs a current.

2. The cell of claim 1, wherein the substrate further comprises a multilayer substrate having a first layer and a second layer underneath the first layer and wherein the one or more microchannels further comprises an upper microchannel in the first layer and a lower microchannel in the second layer.

3. The cell of claim 2, wherein the electrode is adjacent the lower microchannel so that charged electromagnetically sensitive particles in the lower microchannel release their charge to the electrode.

4. The cell of claim 1 further comprises one or more start-up power cells that provide power to the micromechanical pump during an initial operation period of the cell.

5. The cell of claim 1, wherein the electromagnetically sensitive particles further comprises infrared sensitive particles or visible electromagnetically sensitive particles.

6. The cell of claim 1, wherein the electromagnetically sensitive particles further comprises infrared sensitive particles and visible electromagnetically sensitive particles.

7. The cell of claim 1 further comprising a fluid input/output port through which the fluid may be removed from the cell.

8. The cell of claim 1 further comprising a contact, on an exterior surface of the substrate, connected to the electrode.

9. The cell of claim 1, wherein the substrate is silicon.

10. An apparatus, comprising:
a device powered by electrical energy; and
a nano power cell that provides the electrical energy to the device, the nano power cell further comprising a substrate, one or more microchannels formed in the substrate, a pump that circulates a fluid through the microchannels, the fluid containing a plurality of electromagnetically sensitive particles that receive a charge from an electromagnetic radiation source, and an electrode within the substrate that receives the charge from the electromagnetically sensitive particles and outputs a current.

11. The apparatus of claim 10, wherein the device further comprises a mobile phone, a medical device, a portable music device or night vision goggles.

12. A method to generate energy with nano particles in fluid, comprising:
charging a plurality of electromagnetically sensitive nano particles that are suspending in a fluid that is circulating in a microchannel wherein the electromagnetically sensitive nano particles are exposed to an electromagnetic radiation source while in the microchannel; and
discharging the charged electromagnetically sensitive nano particles so that an electric current is generated as the electromagnetically sensitive nano particles circulate in the microchannels.

13. An nano power cell, comprising:
a structure having at least one fiber having an interior channel;
a pump that circulates a fluid through the interior area of the fiber;
the fluid containing a plurality of electromagnetically sensitive particles that receive a charge from an electromagnetic radiation source; and
an electrode within the internal area of the fiber that receives the charge from the electromagnetically sensitive particles and outputs a current.

14. The cell of claim 13 further comprises one or more start-up power cells that provide power to the micromechanical pump during an initial operation period of the cell.

15. The cell of claim 13, wherein the electromagnetically sensitive particles further comprises infrared sensitive particles or visible electromagnetically sensitive particles.

16. The cell of claim 13, wherein the electromagnetically sensitive particles further comprises infrared sensitive particles and visible electromagnetically sensitive particles.

17. The cell of claim 13 further comprising a fluid input/output port through which the fluid may be removed from the cell.

18. The cell of claim 13, wherein the structure is a fabric woven using the at least one fiber.

* * * * *